(12) United States Patent
Li et al.

(10) Patent No.: US 11,046,888 B2
(45) Date of Patent: Jun. 29, 2021

(54) DIFLUOROMETHOXY-BRIDGE LIQUID CRYSTAL COMPOUND CONTAINING METHYL-SUBSTITUTED 2,3-DIFLUOROPHENYL AND CRYSTAL COMPOSITION

(71) Applicant: Shijiazhuang Chengzhi Yonghua Display Material Co., Ltd, Shijiazhuang (CN)

(72) Inventors: Ming Li, Shijiazhuang (CN); Guoliang Yun, Shijiazhuang (CN); Jinsong Meng, Shijiazhuang (CN); Lei Zhao, Shijiazhuang (CN); Hubo Zhang, Shijiazhuang (CN); Wenfei Liu, Shijiazhuang (CN); Zhengqiang Li, Shijiazhuang (CN)

(73) Assignee: Shijiazhuang Chengzhi Yonghua Display Material Co., Ltd., Shijiazhuang (CN)

( * ) Notice: Subject to any disclaimer, the term of this patent is extended or adjusted under 35 U.S.C. 154(b) by 145 days.

(21) Appl. No.: 16/239,306

(22) Filed: Jan. 3, 2019

(65) Prior Publication Data
US 2019/0345388 A1    Nov. 14, 2019

(30) Foreign Application Priority Data
May 11, 2018 (CN) .......................... 201810448524.5

(51) Int. Cl.
| | |
|---|---|
| *G02F 1/1333* | (2006.01) |
| *C09K 19/34* | (2006.01) |
| *C09K 19/30* | (2006.01) |
| *C07C 43/205* | (2006.01) |
| *C09K 19/04* | (2006.01) |

(52) U.S. Cl.
CPC ........ *C09K 19/3402* (2013.01); *C07C 43/205* (2013.01); *C09K 19/3003* (2013.01); *C09K 19/3066* (2013.01); *C09K 2019/0466* (2013.01); *C09K 2019/301* (2013.01); *C09K 2019/3004* (2013.01); *C09K 2019/3016* (2013.01); *C09K 2019/3422* (2013.01)

(58) Field of Classification Search
CPC ............ C09K 19/3402; C09K 19/3066; C09K 2019/0466; C09K 2019/3004; C09K 2019/301; C09K 2019/3016; C09K 2019/3422; G02F 1/1333; C07C 43/205
USPC .................................................... 252/299.61
See application file for complete search history.

(56) References Cited

U.S. PATENT DOCUMENTS 7,981,486 B2 *   7/2011   Sasada ................... C09K 19/20
                                                          428/1.1

* cited by examiner

*Primary Examiner* — Geraldina Visconti
(74) *Attorney, Agent, or Firm* — Muncy, Geissler, Olds & Lowe, P.C.

(57) ABSTRACT

Provided are a difluoromethoxy-bridge liquid crystal compound containing methyl-substituted 2,3-difluorophenyl, a liquid crystal composition containing the compound, and a liquid crystal display element and a liquid crystal display, wherein said liquid crystal composition is represented by the following formula I:

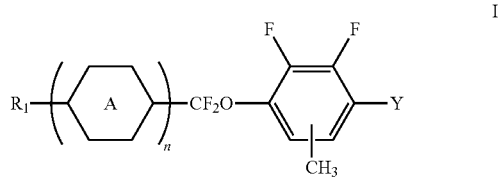

wherein the difluoromethoxy-bridge liquid crystal compound containing methyl-substituted 2,3-difluorophenyl not only has a high clearing point (CP) and a prominent low-temperature miscibility with other liquid crystals, but also has a good stability to ultraviolet light, stability to high temperatures, and particularly also a high vertical dielectric constant ($\varepsilon_\perp$), and may be applied to the formulation of various types of liquid crystal compositions, and it is particularly prominent that the compound has the advantages of both a good low-temperature miscibility and a high vertical dielectric constant ($\varepsilon_\perp$).

10 Claims, 1 Drawing Sheet

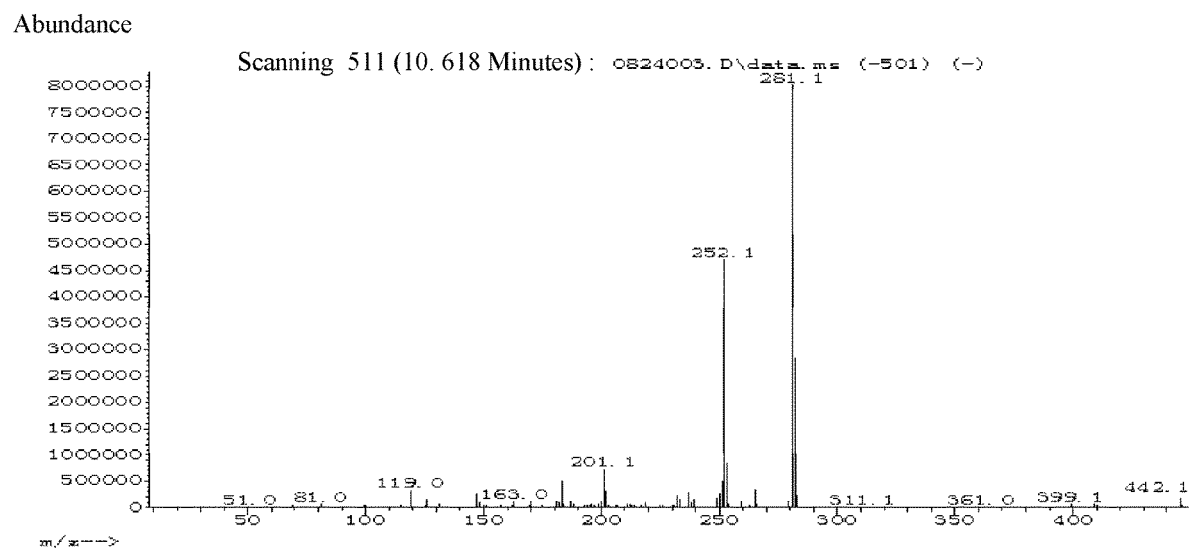

DIFLUOROMETHOXY-BRIDGE LIQUID CRYSTAL COMPOUND CONTAINING METHYL-SUBSTITUTED 2,3-DIFLUOROPHENYL AND CRYSTAL COMPOSITION

TECHNICAL FIELD

The present invention belongs to the field of liquid crystalline compounds, and in particular relates to a difluoromethoxy-bridge liquid crystal compound containing methyl-substituted 2,3-difluorophenyl, a liquid crystal composition, and a liquid crystal display element or liquid crystal display comprising the liquid crystal compound or the liquid crystal composition.

BACKGROUND ART

The use of a liquid crystal compound as a display material has obvious advantages such as a low drive voltage, a small power consumption, a high reliability, a large amount of display information, a colour display, no flicker, being capable of realizing a flat panel display, etc. In order to enable the performance of liquid crystal display elements and liquid crystal displays to be more optimized, efforts have been made to study new liquid crystal compounds. At present, it is known that there are more than 10,000 liquid crystal materials, among which there are thousands of commonly used liquid crystal display materials, and according to the characteristics of the central bridge linkages and rings of the liquid crystal molecules, the liquid crystals are mainly classified into biphenyl liquid crystals, phenylcyclohexane liquid crystals, ester liquid crystals, acetylene liquid crystals, difluoromethoxy bridge liquid crystals, ethane liquid crystals, heterocyclic liquid crystals, etc.

Studies have shown that the rotary viscosity $\gamma_1$ of a liquid crystal molecule containing a difluoromethoxy bridge (—$CF_2O$—) is lowered. In addition, due to the contribution of the dipole moment of the difluoromethoxy bridge (—$CF_2O$—), the dipole moment of the terminal fluorine atom also increases to some extent, thereby increasing the dielectric anisotropy $\Delta\varepsilon$ of the liquid crystal molecule.

CN 105131971 A discloses a liquid crystal compound containing a difluoromethoxy bridge as represented by the following formula:

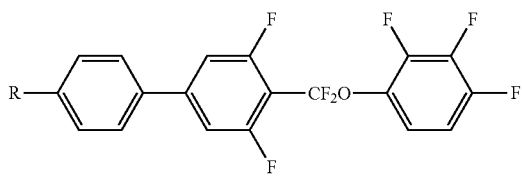

Although the liquid crystal compound has a large dielectric anisotropy and a low rotary viscosity ($\gamma_1$), the clearing point thereof is lower, and in the formulation of a liquid crystal mixture, it is necessary to add a high-clearing point compound with a larger viscosity to balance the decrease of the clearing point caused by the (—$CF_2O$—) group, thereby restricting the room for improving the response speed of the liquid crystal mixture. Furthermore, there is still room for improvement in the low-temperature miscibility, vertical dielectric constant, etc., of the liquid crystal compound.

In addition, with the development of technologies, the liquid crystal composition is required to be also able to work at a very low temperature, especially in an outdoor environment, for example, to work in an outdoor environment of −30° C. or less for a long period of time, which requires the liquid crystal composition to have good low-temperature properties, that is to say, a liquid crystal monomer is required not to precipitate even when stored at a low temperature for a long period of time, so it is still necessary to develop a liquid crystal having a good miscibility at a low temperature.

In addition, liquid crystal display devices tend to be designed to have a high pixel density, and for the control of the power consumption of a backlight, the requirements for the light transmittance of a liquid crystal layer are also increasing, so the development of a liquid crystal with a high transmittance is currently one of the important liquid crystal development directions.

SUMMARY OF THE INVENTION

An object of the present invention is to provide a difluoromethoxy-bridge liquid crystal compound containing methyl-substituted 2,3-difluorophenyl. Furthermore, another object of the present invention is to provide a liquid crystal composition comprising a difluoromethoxy-bridge liquid crystal compound containing methyl-substituted 2,3-difluorophenyl. Furthermore, another object of the present invention is to provide a liquid crystal display element or liquid crystal display. Said liquid crystal composition also has an improved low-temperature miscibility and an improved vertical dielectric constant while maintaining a good rotational viscosity and clearing point.

In order to achieve the above-mentioned objects, the present inventors have intensively studied and found a novel difluoromethoxy-bridge liquid crystal compound containing methyl-substituted 2,3-difluorophenyl, which can solve the technical problem of the present invention, to accomplish the present invention.

In particular, the present invention relates to a difluoromethoxy-bridge liquid crystal compound containing methyl-substituted 2,3-difluorophenyl, which is represented by formula I below:

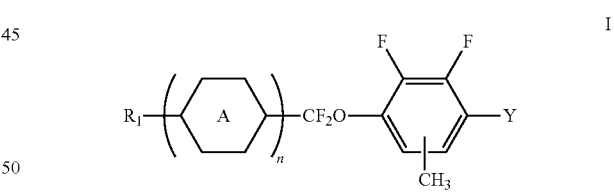

wherein $R_1$ represents H, an alkyl group having a carbon atom number of 1-5, an alkenyl group having a carbon atom number of 2-6 or an alkoxy group having a carbon atom number of 1-5, with any $CH_2$ in $R_1$ being optionally substituted with cyclopentyl, cyclobutyl or cyclopropyl, any $CH_2$ not connected to O being optionally substituted with O and any one or more hydrogen atoms being optionally substituted with a fluorine atom;

n represents 1, 2, 3 or 4; and

Y represents H, F, Cl, CN, an alkyl group having a carbon atom number of 1-5, an alkenyl group having a carbon atom number of 2-6 or an alkoxy group having a carbon atom number of 1-5, with any CH2 not connected to O being optionally substituted with O and any one or more hydrogen atoms being optionally substituted with a fluorine atom;

represents one or more of phenylene, a fluoro-substituted phenylene group, cyclohexenylene, cyclohexylene and a group formed by substituting one or two non-connected CH$_2$ in cyclohexylene with O;

and

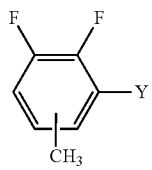

represents

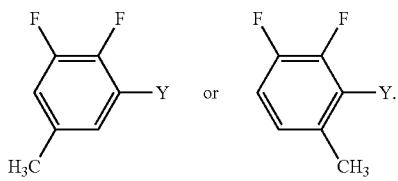

The above-mentioned difluoromethoxy-bridge liquid crystal compound containing methyl-substituted 2,3-difluorophenyl has a high clearing point (CP), a prominent low-temperature miscibility with other liquid crystals and a high vertical dielectric constant ($\varepsilon_\perp$), and may be applied to the formulation of various types of liquid crystal compositions, and it is particularly prominent that the compound has both a good low-temperature miscibility and a high vertical dielectric constant ($\varepsilon_\perp$). In addition, it further has a good stability to ultraviolet light and a good stability to high temperatures.

The above-mentioned difluoromethoxy-bridge liquid crystal compound containing methyl-substituted 2,3-difluorophenyl itself is colourless, may be used for the formulation of a positive liquid crystal composition for display devices of various modes, such as OCB, TN, STN, IPS and FFS, and thus has a wider range of applications.

The above-mentioned difluoromethoxy-bridge liquid crystal compound containing methyl-substituted 2,3-difluorophenyl can be used as a base material of a liquid crystal composition, or may also be used as an additive material to be added to a liquid crystal composition with another type of compound as a liquid crystal base material, enabling the liquid crystal composition to attain one or more of the properties of an improved low-temperature miscibility, a vertical dielectric constant, a dielectric anisotropy $\Delta\varepsilon$, a rotatory viscosity $\gamma_1$, a threshold voltage $V_{th}$, a contrast at low temperatures, an optical anisotropy $\Delta n$, a clearing point Cp, etc.

In the above-mentioned difluoromethoxy-bridge liquid crystal compound containing methyl-substituted 2,3-difluorophenyl, the compound represented by formula I is preferably a compound represented by formulas I1-I18

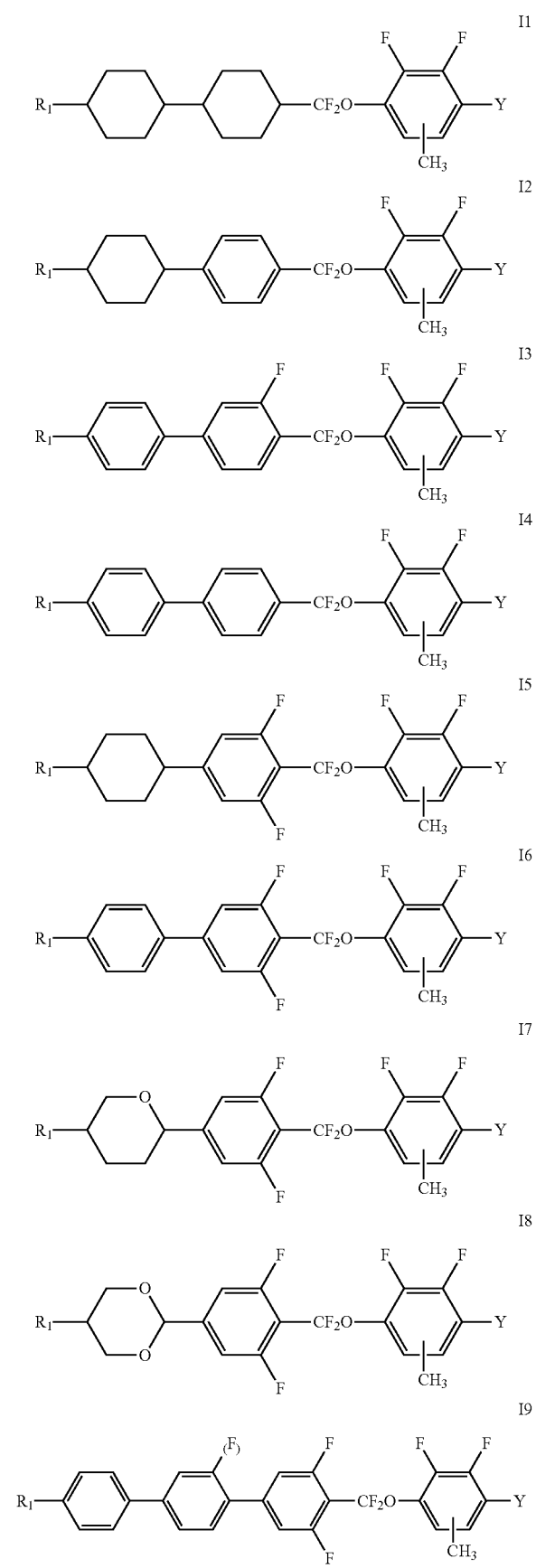

I10
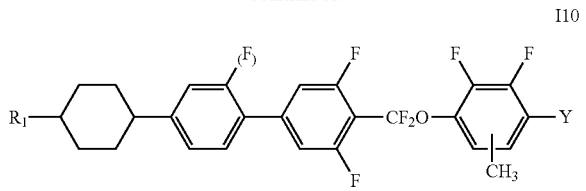

I11
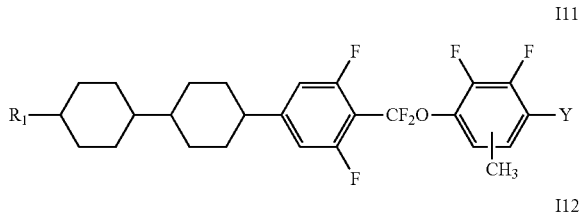

I12
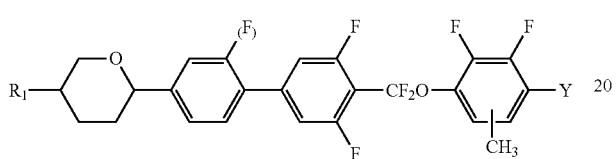

I13

I14
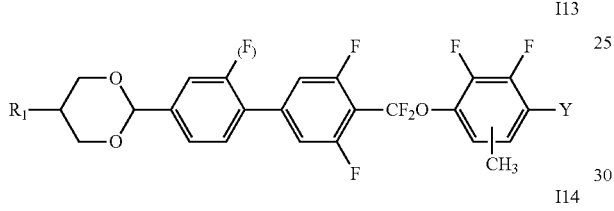

I15
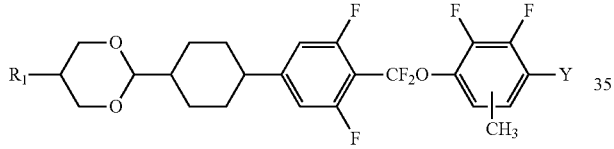

I16
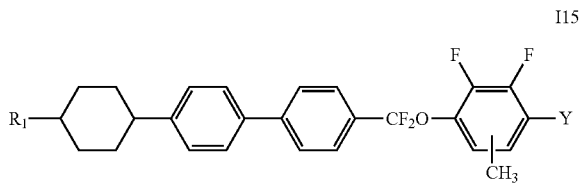

I17
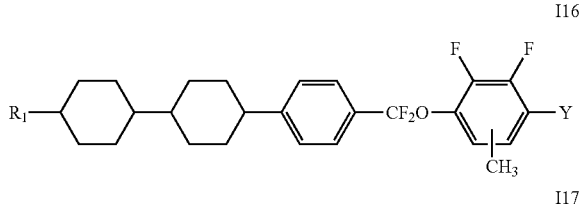

I18
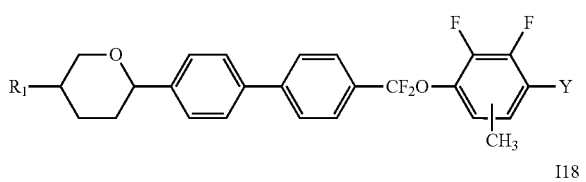

wherein $R_1$ represents H, an alkyl group having a carbon atom number of 1-5, an alkenyl group having a carbon atom number of 2-6 or an alkoxy group having a carbon atom number of 1-5, with any $CH_2$ in $R_1$ being optionally substituted with cyclopentyl, cyclobutyl or cyclopropyl, any $CH_2$ not connected to O being optionally substituted with O and any one or more hydrogen atoms being optionally substituted with a fluorine atom;

Y represents H, F, Cl, CN, or an alkyl group having a carbon atom number of 1-5, an alkenyl group having a carbon atom number of 2-6 or an alkoxy group having a carbon atom number of 1-5, with any $CH_2$ not connected to O being optionally substituted with O and any one or more hydrogen atoms being optionally substituted with a fluorine atom;

and

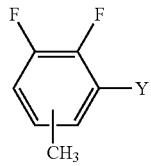

represents

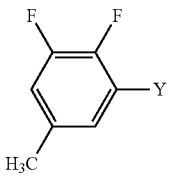 or 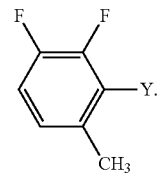

The difluoromethoxy-bridge liquid crystal compound containing methyl-substituted 2,3-difluorophenyl, as represented by formula I1-I18, has a particularly prominent vertical dielectric constant ($\varepsilon_\perp$), a good low-temperature miscibility with other liquid crystals, a good stability to ultraviolet light and a stability to high temperatures.

When various variables tend to have a large or small polarization in the long-axis direction of the molecule, the difluoromethoxy-bridge liquid crystal compound containing methyl-substituted 2,3-difluorophenyl, as represented by formula I1-I18, can achieve a value of a dielectric anisotropy ($\Delta\varepsilon$) within a range between 0 and 20, while having a lower rotatory viscosity ($\gamma1$); according to the degree of conjugation of liquid crystal molecules of various structures, the optical anisotropy ($\Delta n$) can achieve a value range between 0.05 and 0.35; according to the number of ring A and different substituents, the clearing point may achieve a range of 20° C. and 200° C.; and the compound represented by formulae I1-I18 also has a good low-temperature miscibility with other liquid crystals, and may improve the low-temperature characteristics of a mixed liquid crystal. The structure of the methyl-substituted 2,3-difluorophenyl has an improved low-temperature miscibility and an increased vertical dielectric constant while maintaining a good rotatory viscosity and a clearing point, as compared with existing 2,3-difluorophenyl parallel to the long-axis of the molecule. In addition, a liquid crystal compound containing a halogen element such as bromine or iodine is unstable under high temperature and UV conditions, which may result in reduced electrooptical properties after a long-time service. The compound represented by formula I does not contain any halogen element such as bromine or iodine, and thus has the advantage that the electrooptical properties thereof do not decrease even in the case of service in a high-temperature and UV environment for a long time, as compared with liquid crystal compounds containing a halogen element such as bromine or iodine. The present invention further relates to a liquid crystal composition comprising one or more difluoromethoxy-bridge liquid crystal compounds containing methyl-substituted 2,3-difluorophenyl, as represented by formula I.

The present invention further relates to a liquid crystal composition comprising one or more difluoromethoxy-bridge liquid crystal compounds containing methyl-substituted 2,3-difluorophenyl, as represented by formula I1-I18.

The liquid crystal composition of the present invention preferably further comprises one or more compounds represented by formula II.

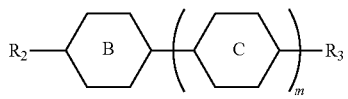

II wherein $R_2$ and $R_3$ each independently represent an alkyl group having a carbon atom number of 1-5, an alkenyl group having a carbon atom number of 2-6 or an alkoxy group having a carbon atom number of 1-5;

m represents 1 or 2;

and

and

each independently represent one or more selected from phenylene, cyclohexylene and/or cyclohexenylene.

In the liquid crystal composition of the present invention, it is preferable that the content in mass percentage of the compound represented by formula I is 1-40%, further preferably 2-30%, more preferably 5-20%. It is preferable that the content in mass percentage of the compound represented by formula II is 1-65%, further preferably 10-55%, more preferably 30-50%. It should be noted that the term "content" in the present application refers to a content in mass percentage, the same hereinafter.

Within this content range, a composition formed from the compounds of formula I and formula II not only can maintain a larger vertical dielectric constant ($\varepsilon_\perp$), a lower rotatory viscosity ($\gamma_1$) and a higher clearing point (Cp), but also can have a good low-temperature stability.

In the liquid crystal composition of the present invention, said one or more compounds represented by formula I are preferably one or more of compounds represented by formulas II1 to II22 below:

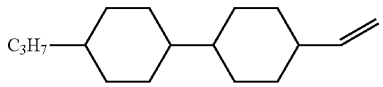 II1

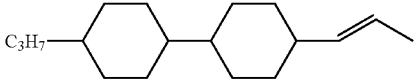 II2

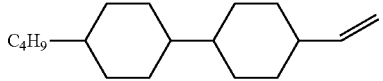 II3

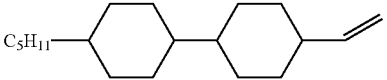 II4

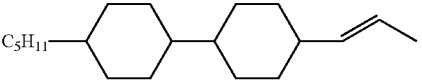 II5

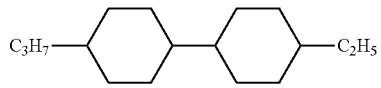 II6

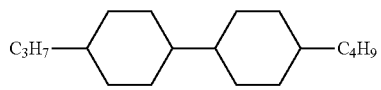 II7

 II8

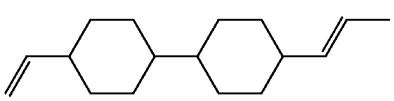 II9

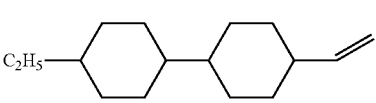 II10

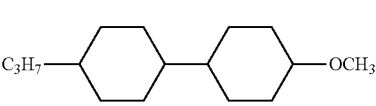 II11

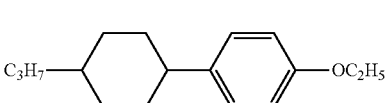 II12

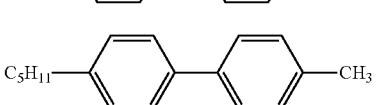 II13

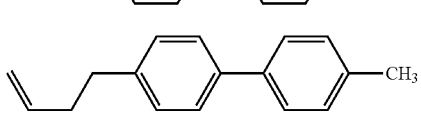 II14

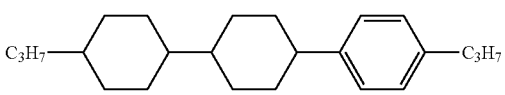 II15

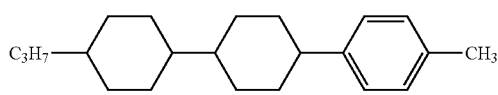 II16

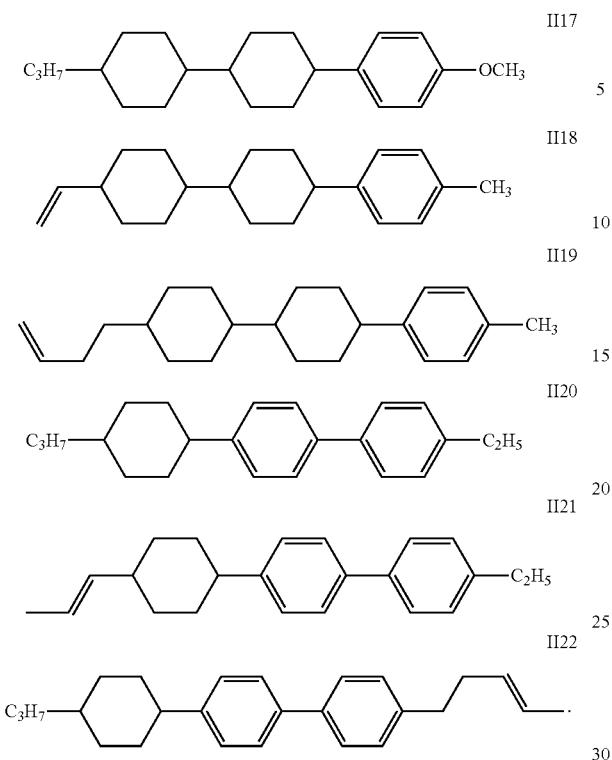
The liquid crystal composition of the present invention may further comprise one or more of compounds represented by formulas III1 to III14 below:
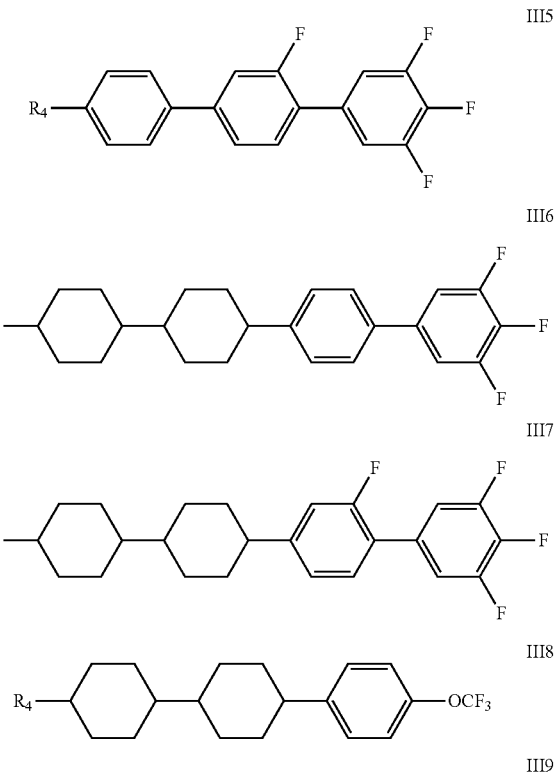
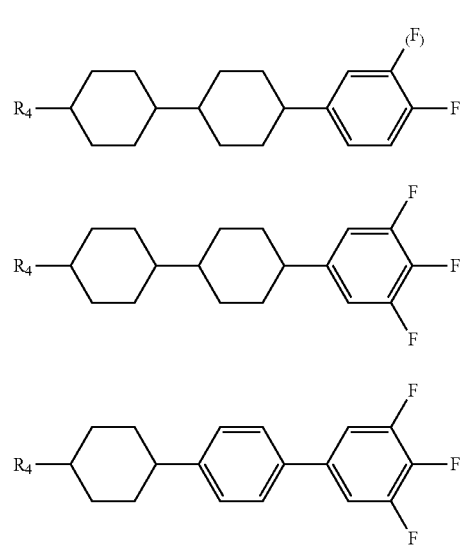
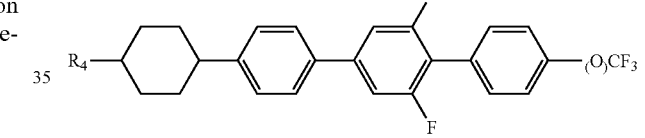
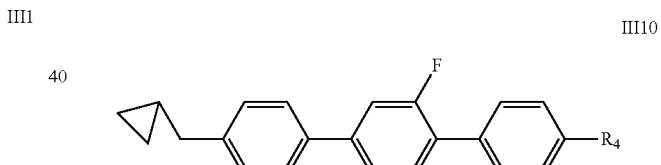
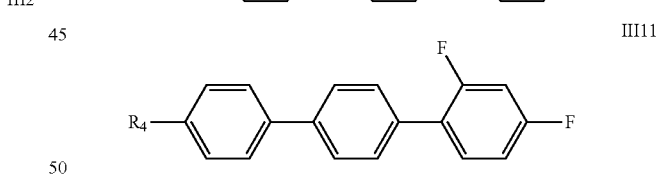
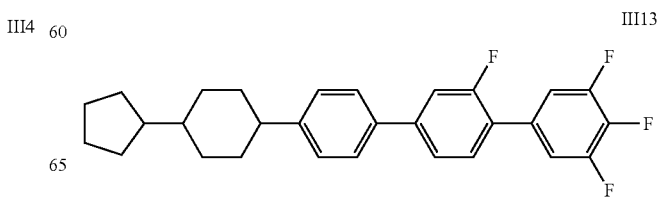

-continued

III14

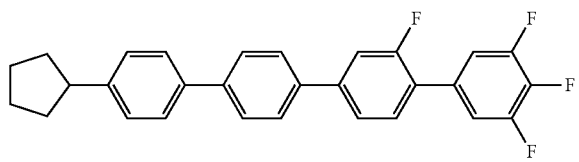

wherein each $R_4$ independently represents H, an alkyl group having a carbon atom number of 1-5, an alkenyl group having a carbon atom number of 2-6 or an alkoxy group having a carbon atom number of 1-5, with any $CH_2$ in $R_4$ being optionally substituted with cyclopentyl, cyclobutyl or cyclopropyl;

(F) represents F or H;

and (O) represents —O— or a single bond.

The liquid crystal composition of the present invention may further comprise one or more compounds represented by formula IV:

IV

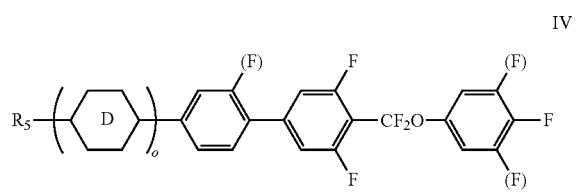

$R_5$ represents H, an alkyl group having a carbon atom number of 1-5, an alkenyl group having a carbon atom number of 2-6 or an alkoxy group having a carbon atom number of 1-5, with any $CH_2$ in $R_5$ being optionally substituted with cyclopentyl, cyclobutyl or cyclopropyl;

o represents 0 or 1;

represents phenylene, cyclohexylene, cyclohexenylene or a group formed by substituting one or two non-connected $CH_2$ in cyclohexylene with O;

and (F) each independently represent H or F.

The compound represented by formula IV is preferably one or more of compounds represented by formulas IV1 to IV15:

IV1

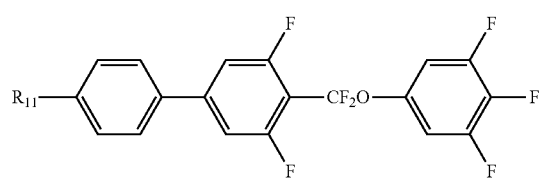

-continued

IV2

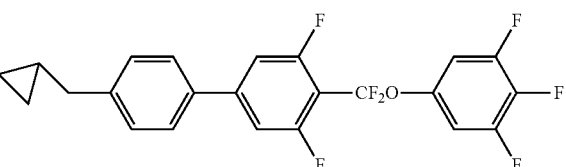

IV3

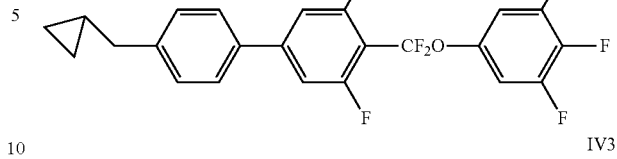

IV4

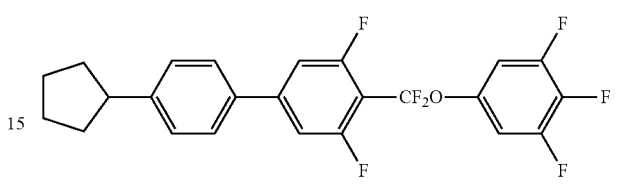

IV5

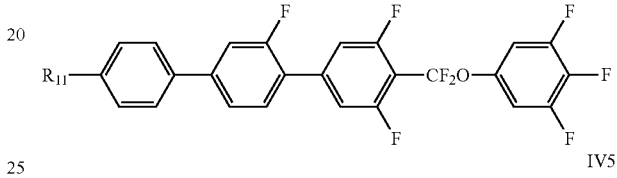

IV6

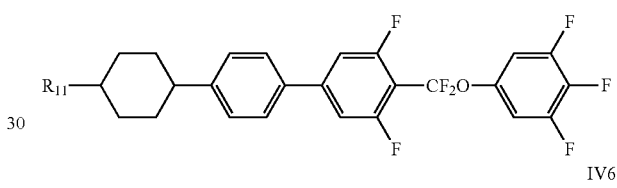

IV7

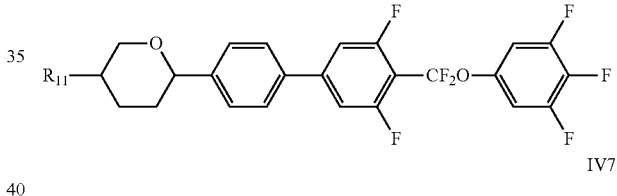

IV8

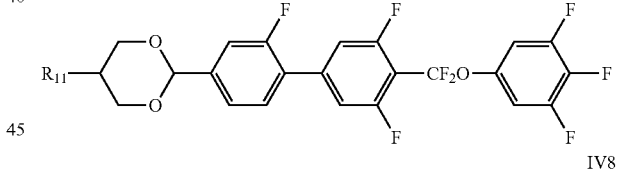

IV9

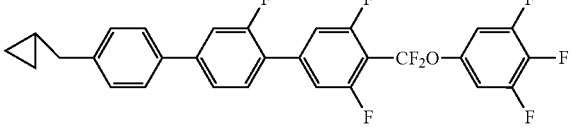

IV10

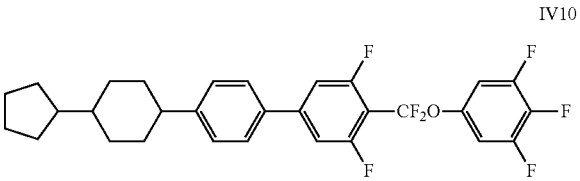

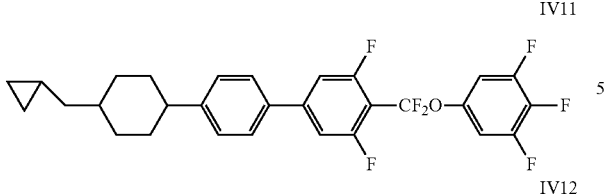
IV11

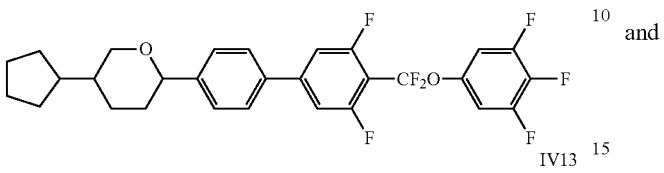
IV12

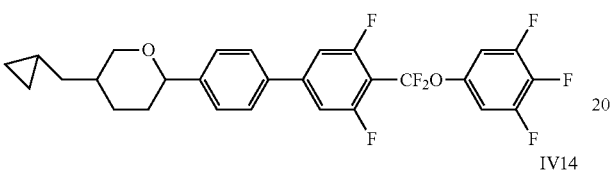
IV13

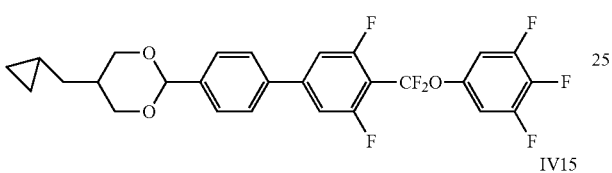
IV14

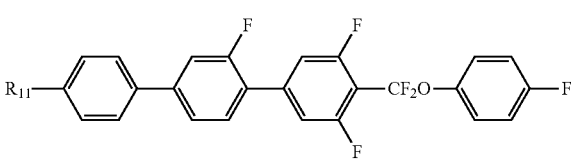
IV15

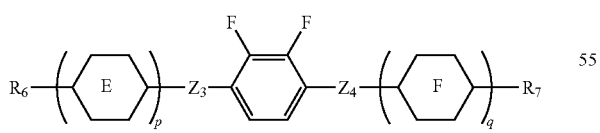

wherein each $R_{11}$ independently represents H, an alkyl group having a carbon atom number of 1-5, an alkenyl group having a carbon atom number of 2-6 or an alkoxy group having a carbon atom number of 1-5, with any $CH_2$ in $R_{11}$ being optionally substituted with cyclopentyl, cyclobutyl or cyclopropyl.

The compound of formula IV has a larger dielectric anisotropy and can be used to adjust the drive voltage.

In the liquid crystal composition of the present invention, a negative liquid crystal component can be further added: one or more negative compounds represented by formula V below,

V

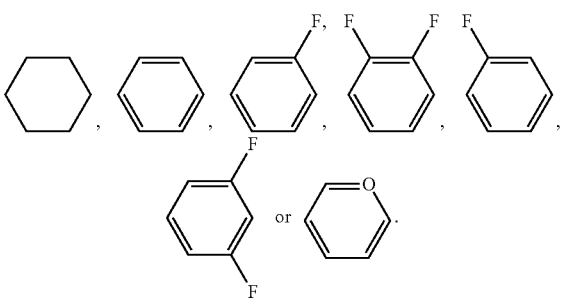

wherein $R_6$ and $R_7$ represent H, an alkyl group having a carbon atom number of 1-5, an alkenyl group having a carbon atom number of 2-6 or an alkoxy group having a carbon atom number of 1-5, with any $CH_2$ in $R_6$ and $R_7$ being optionally substituted with cyclopentyl, cyclobutyl or cyclopropyl;

p and q each independently represent 0, 1 or 2, with $1 \leq p+q \leq 3$;

$Z_3$ and $Z_4$ each independently represent a single bond, $-CH_2CH_2-$, $-CH_2O-$ or $-OCH_2-$; and

and

each independently represent

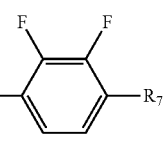

In the liquid crystal composition of the present invention, the negative compound represented by formula V is preferably a compound represented by formulas V1-V13 below:

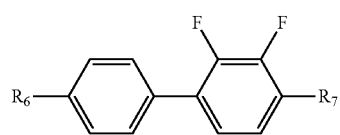
V1

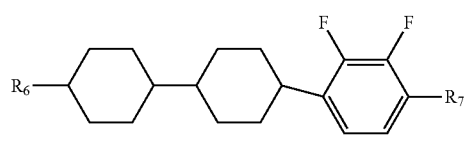
V2

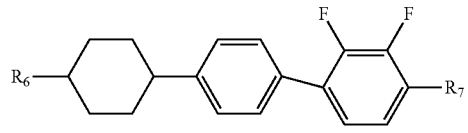
V3

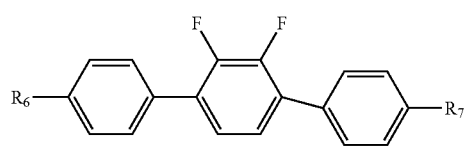
V4

V5

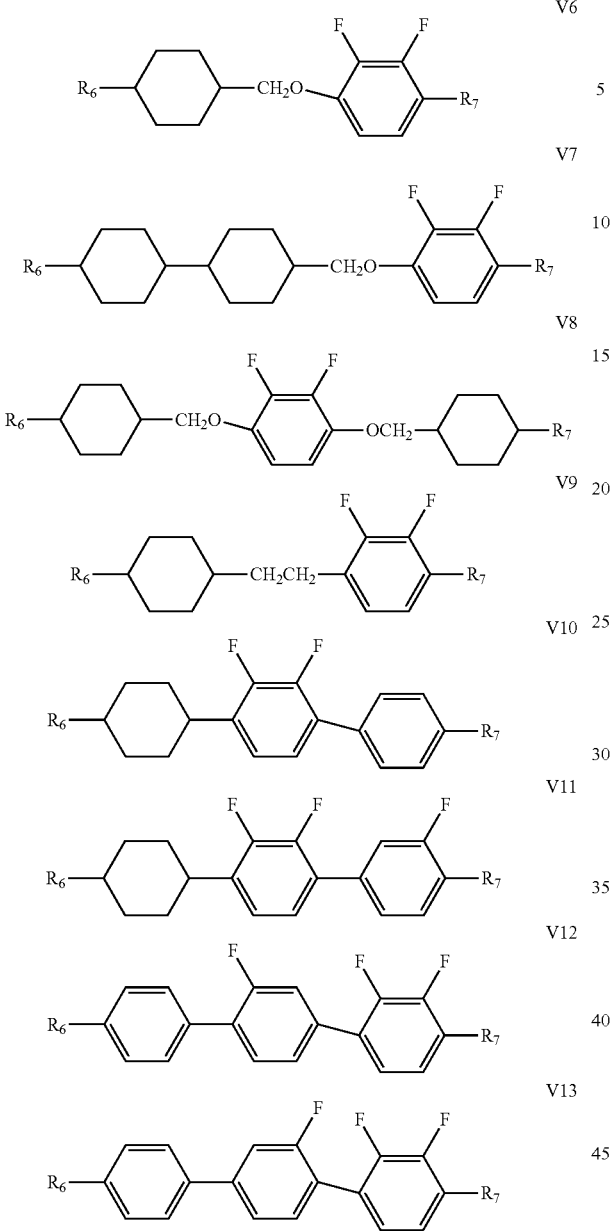

The liquid crystal composition of the present invention may further comprise one or more compounds represented by formula VI,

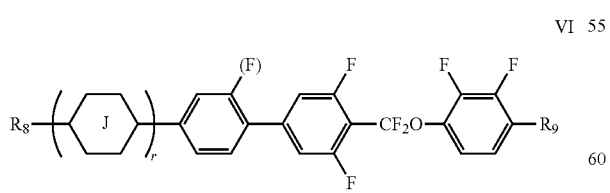

wherein $R_8$ represents H, an alkyl group having a carbon atom number of 1-5, an alkenyl group having a carbon atom number of 2-6 or an alkoxy group having a carbon atom number of 1-5, with any $CH_2$ in $R_8$ being optionally substituted with cyclopentyl, cyclobutyl or cyclopropyl;

represents phenylene, cyclohexylene, cyclohexenylene or a group formed by substituting one or two non-connected $CH_2$ in cyclohexylene with O;

r represents 0 or 1;

(F) represents F or H;

and $R_9$ represents F, an alkyl group having a carbon atom number of 1-6 or an alkoxy group having a carbon atom number of 1-6.

The compound represented by formula VI is preferably selected from the group consisting of compounds represented by formulas VI1 to VI10 below:

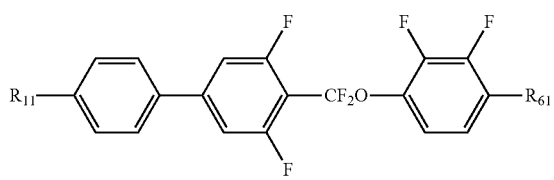

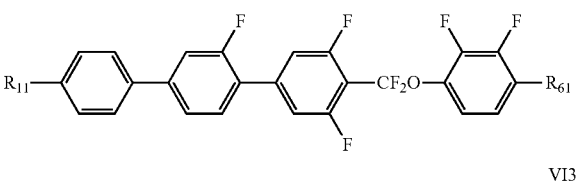

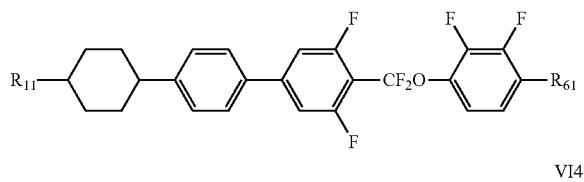

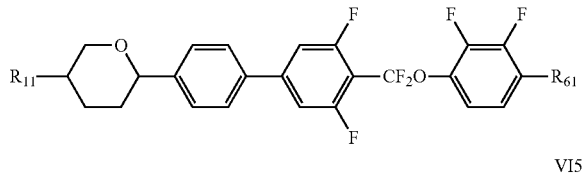

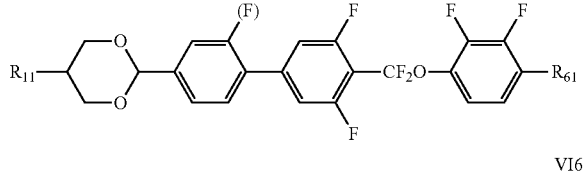

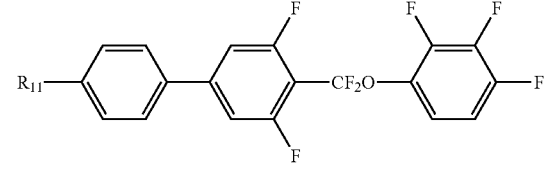

-continued

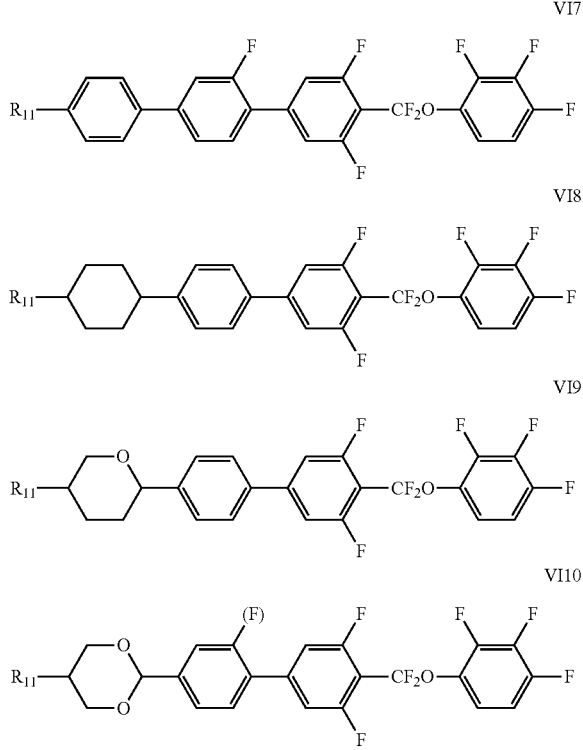

wherein each $R_{11}$ independently represents an alkyl group having a carbon atom number of 1-6;

(F) represents F or H;

and each $R_{61}$ independently represents an alkyl group having a carbon atom number of 1-6 or an alkoxy group having a carbon atom number of 1-6.

The liquid crystal composition of the present invention has a wider range of dielectric anisotropy (Δε), which may achieve a numerical value between 2 and 20, an appropriate optical anisotropy (Δn), which may achieve a numerical value between 0.060 and 0.300, a good low-temperature miscibility with other liquid crystals, a low rotary viscosity ($\gamma_1$), e.g., 150 mPa·s or less, or even as low as 40 mPa·s, a higher clearing point (CP), which may achieve, for example, a numerical value between 60° C. and 120° C., and a good stability to ultraviolet light and a good stability to high temperatures, and thus can be applied to various display modes and can satisfy the requirements for the liquid crystal properties, such as different cell thicknesses, fast responses, different drive voltages and low viscosities for various display modes.

The present invention further relates to a liquid crystal display element or liquid crystal display comprising the above-mentioned liquid crystal composition. Said liquid crystal display element or liquid crystal display may be in a mode of IPS, FFS, TN, STN, etc.

To the liquid crystal composition of the present invention, a left-hand or right-hand chiral dopant may be further added to form a chiral nematic phase.

The liquid crystal or trace impurities therein easily form into an excited state or even easily form free radicals after being irradiated with a high temperature, ultraviolet light or visible light, and the chemical properties in the excited state or of the free radicals are active, which may cause chemical reactions that lead to reduced liquid crystal quality, e.g., an oxidation reaction, to occur. During the synthesis and use of the liquid crystal compound of the present invention, various functional dopants can be further added, wherein the contents of the dopants are preferably between 0.01% and 1%, and these dopants are mainly an antioxidant, an ultraviolet absorber and a light stabilizer, to be used for improving the stability and quality of the liquid crystal and extending the service time of the mixed liquid crystal.

The antioxidant, ultraviolet absorber, and light stabilizer are preferably substances listed below:

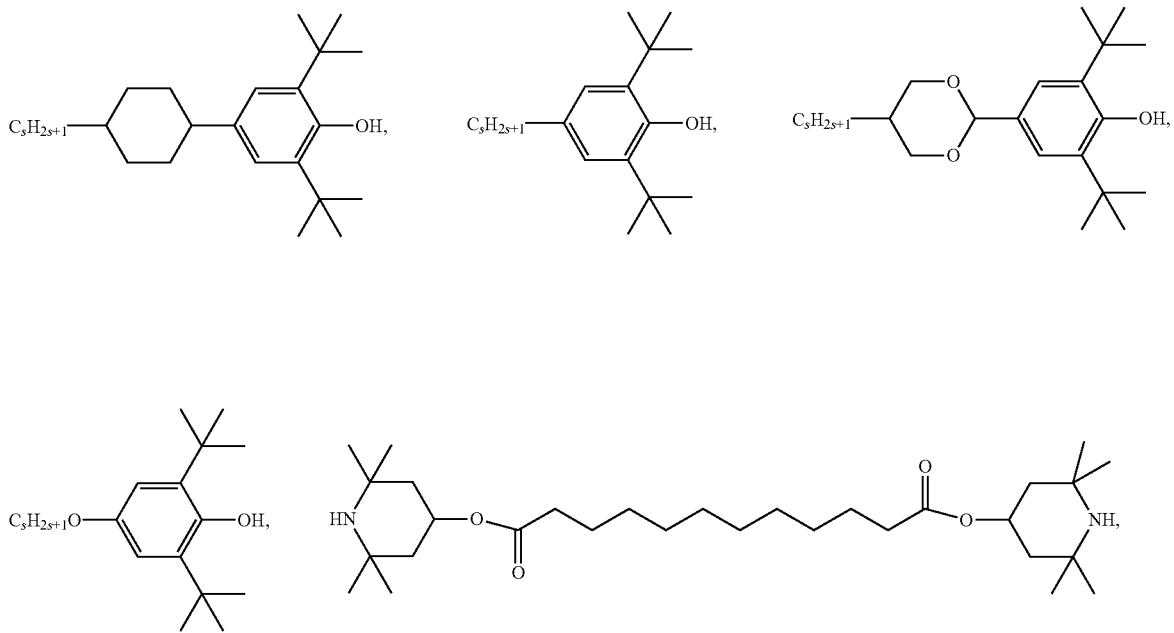

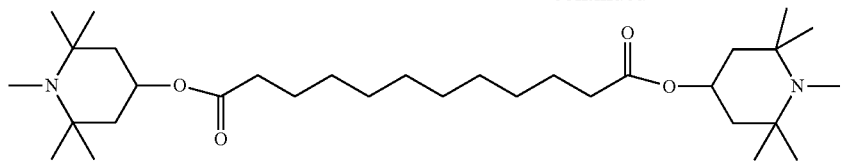

with S being an integer selected from 1 to 10.

BRIEF DESCRIPTION OF THE DRAWINGS

The sole FIGURE is a mass spectrum of a PUQYi-3-F compound in Example 1.

DETAILED DESCRIPTION OF EMBODIMENTS

The present invention is further described in conjunction with particular examples below, but the present invention is not limited to the following examples. Said methods are all conventional methods, unless otherwise specified.

The specific meanings of symbols and the test conditions in the examples are as follows:

Cp: represents the clearing point of a liquid crystal, with a unit of ° C.

S-N: represents the melting point of a liquid crystal from a crystal state to a nematic phase, with a unit of ° C.

Δn: represents optical anisotropy, with $\Delta n = n_o - n_e$, in which $n_o$ is the refractive index of an ordinary light, and $n_e$ is the refractive index of an extraordinary light, with the test conditions being 589 nm and 25±0.5° C.

Δε: dielectric anisotropy, with $\Delta\varepsilon = \varepsilon_{//} - \varepsilon_\perp$, in which $\varepsilon_{//}$ is the dielectric constant parallel to the molecular axis, and $\varepsilon_\perp$ is the dielectric constant perpendicular to the molecular axis, with the test conditions being 25±0.5° C., 1 KHz, HP4284A, and a 5.2 μm TN left-hand cell.

$\gamma_1$: rotatory viscosity, with a unit of mPa·s, the test conditions being 25±0.5° C.

VHR: voltage holding ratio (%), with the test conditions being 20±2° C., a voltage of ±5 V, a pulse width of 10 ms, and a voltage holding time of 16.7 ms. The test equipment is a TOYO Model 6254 liquid crystal performance comprehensive tester.

It should be noted that the process of the subsequent reaction for the synthesis of a liquid crystal compound is generally monitored by means of TLC, and treatments after the completion of the reaction are generally water washing, extraction, organic phase combination and drying, solvent evaporation under reduced pressure, as well as recrystallization and column chromatography; and a person skilled in the art would be able to implement the present invention according to the following description.

The synthesis route of the compound represented by formula I is

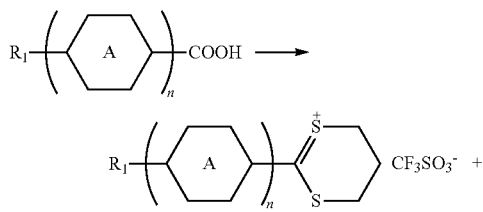

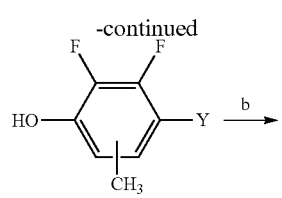

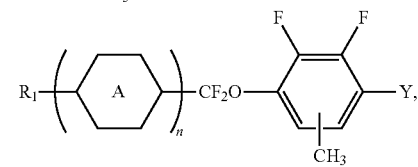

and specifically comprises the following two steps, i.e., steps a and b, a) a raw material

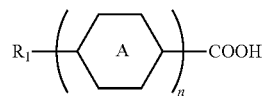

is dissolved in toluene,

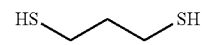

is added, the temperature is raised to 60° C. under stirring, CF$_3$SO$_3$H is dropwise added, the temperature is raised to reflux after the addition is complete, water is separated, a reaction under refluxing is carried out for 12 hours, the temperature is reduced, the toluene is evaporated to dryness, methyl tert-butyl ether is added for washing, and after suction filtration, a product

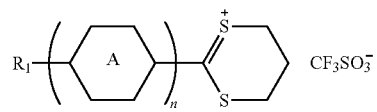

is obtained.

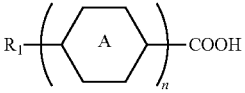

In, $R_1$ represents H, an alkyl group having a carbon atom number of 1-5, an alkenyl group having a carbon atom number of 2-6 or an alkoxy group having a carbon atom number of 1-5, with any CH$_2$ in $R_1$ being optionally substituted with cyclopentyl, cyclobutyl or cyclopropyl, any CH$_2$ not connected to O being optionally substituted with O and any one or more hydrogen atoms being optionally substituted with fluorine atom; n represents 1, 2, 3 or 4;

and represents one or more of phenylene, a fluoro-substituted phenylene group, cyclohexenylene, cyclohexylene and a group formed by substituting one or two non-connected CH$_2$ in cyclohexylene with O.

b) The resulting

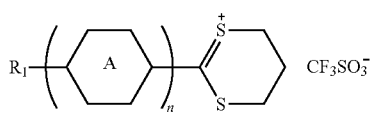

from step a) is dissolved in dichloromethane, the temperature is reduced to −75° C. under the protection of an inert gas, a solution of triethylamine and

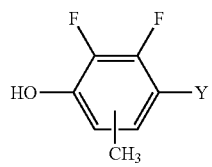

in dichloromethane is dropwise added, a reaction is carried out at a maintained temperature for 1 hour after the addition is complete, triethylamine tris(hydrogen fluoride) is dropwise added, a reaction is carried out at a maintained temperature for 30 minutes after the dropwise addition is complete, Br$_2$ is further dropwise added, a reaction is carried out at a maintained temperature for 30 minutes after the dropwise addition is complete, the temperature is naturally raised to −20° C., the reaction solution is poured to a saturated solution of sodium bicarbonate, and after liquid separation, extraction, water washing, passing through a silica gel column and concentration, a target product

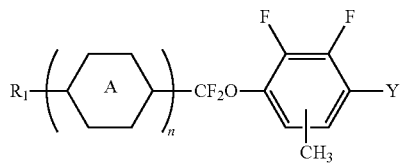

is obtained, wherein

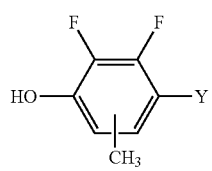

represents

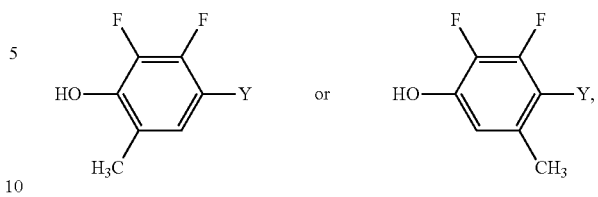

Y represents H, F, Cl, CN, an alkyl group having a carbon atom number of 1-5, an alkenyl group having a carbon atom number of 2-6 or an alkoxy group having a carbon atom number of 1-5, with any CH$_2$ not connected to O being optionally substituted with O and any one or more hydrogen atoms being optionally substituted with a fluorine atom.

The key intermediates

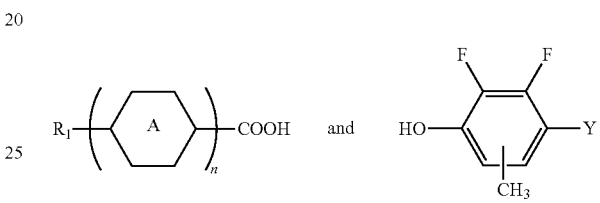

in the synthesis of the compound represented by formula I may be purchased from commercial approaches.

In the examples of the present invention application, liquid crystal monomer structures are represented by codes, wherein the code representation methods of ring structures, end groups and linking groups of the liquid crystals are shown in tables (I) and (II) below

TABLE (I)

| Corresponding code for ring structure | |
| --- | --- |
| Ring structure | Corresponding code |
| (cyclohexane) | C |
| (difluorophenyl) | U |
| (phenyl) | P |
| (tetrahydropyran) | A |
| (fluorophenyl) | G |

TABLE (I)-continued

Corresponding code for ring structure

| Ring structure | Corresponding code |
|---|---|
| 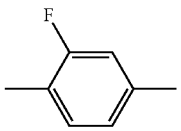 | Gi |
| 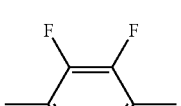 | Y |
| 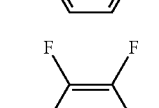 | Yi |
| 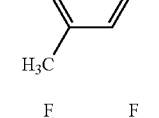 | Yii |

TABLE (II)

Corresponding code for end group and linking group

| End group and linking group | Corresponding code |
|---|---|
| $C_nH_{2n+1}$— | n- |
| $C_nH_{2n+1}O$— | nO— |
| —$OCF_3$ | —OT |
| —$CF_2O$— | —Q— |
| —$CH_2O$— | —O— |
| —F | —F |
| —CN | —CN |
| —$CH_2CH_2$— | —E— |
| —CH=CH— | —V— |
| —C≡C— | —W— |
| —COO— | —COO— |
| —CH=CH—$C_nH_{2n+1}$ | Vn— |
|  | C(5)— |
|  | C(3)1— |

Example

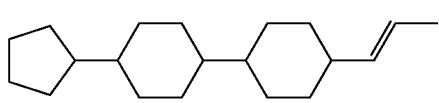

CC-C(5)-VI

-continued

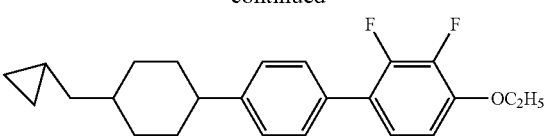

CPY-C(3)1-O2

Example 1

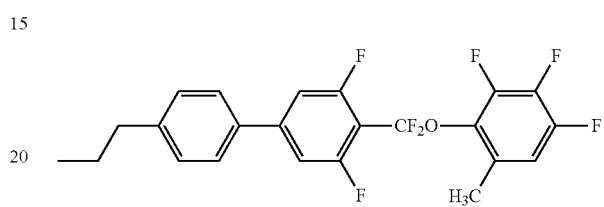

PUQYi-3-F

The synthesis route is:

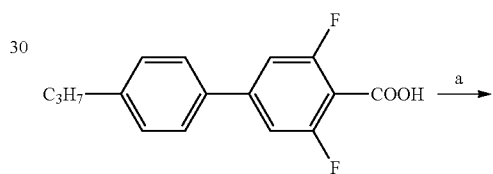

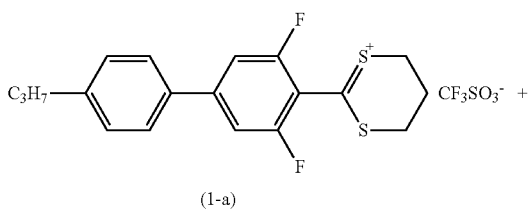

(1-a)

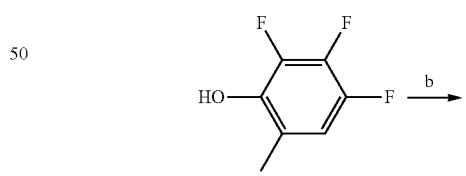

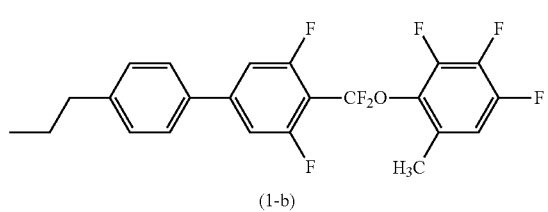

(1-b)

and specifically comprises two steps, i.e., steps 1-a) and 1-b):

1-a) 115 g (0.42 mol) of a raw material

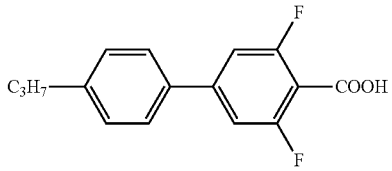

is dissolved in 1.0 L of toluene, 54 g (0.5 mol) of

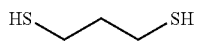

is added, the temperature is raised to 60° C. under stirring, 75 g (0.5 mol) of trifluoromethanesulfonic acid (CF$_3$SO$_3$H) is dropwise added, the temperature is raised to reflux after the addition is complete, water is separated, reaction under refluxing is carried out for 12 hours, the temperature is reduced, the toluene is evaporated to dryness, 0.6 L of methyl tert-butyl ether is added for washing, and after suction filtration, 150 g of a product

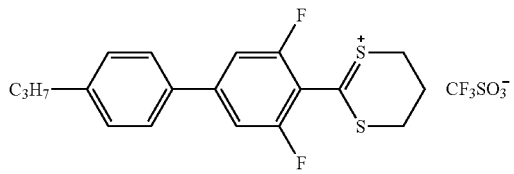

is obtained with a yield of 60%.

1-b) 48 g (0.10 mol) of the resulting

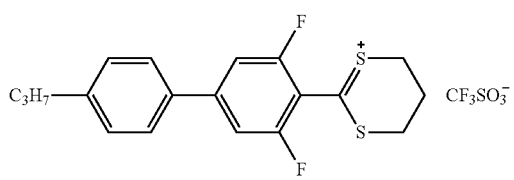

from step 1-a) is dissolved in 0.2 L of dichloromethane, the temperature is reduced to −75° C. under the protection of an inert gas, 0.2 L of a solution of 19.4 g (0.2 mol) of triethylamine and 16.2 g (0.1 mol) of

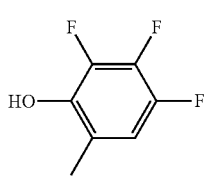

in dichloromethane is dropwise added, a reaction is carried out at a maintained temperature for 1 hour after the addition is complete, 161 g (0.29 mol) of triethylamine tris(hydrogen fluoride) (NEt$_3$.3HF) is dropwise added, a reaction is carried out at a maintained temperature for 30 minutes after the dropwise addition is complete, 32.2 g (0.29 mol) of Br$_2$ is further dropwise added, a reaction is carried out at a maintained temperature for 30 minutes after the dropwise addition is complete, the temperature is naturally raised to −20° C., the reaction solution is poured to 0.4 L of a saturated solution of sodium bicarbonate, and after liquid separation, extraction, water washing, passing through a silica gel column, concentration and recrystallization, 15 g of a target product PUQYi-3-F

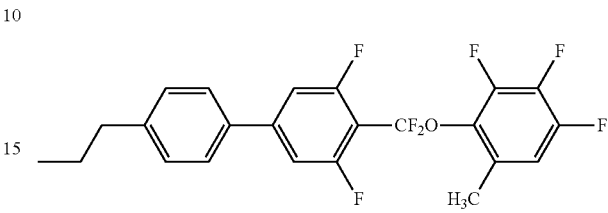

is obtained with GC=99.88% and a yield of 34%.

The parameters of PUQYi-3-F are as follows: Δn=0.1402, Cp=30.5° C., ε$_\perp$=6.8 and Δε=12.0.

The following compound is synthesized in the same manner as in the synthesis method of Example 1, except that the starting materials in Example 1 are replaced, and the synthesis method therefor will not be repeated below:

Example 2 PUQYi-2-F

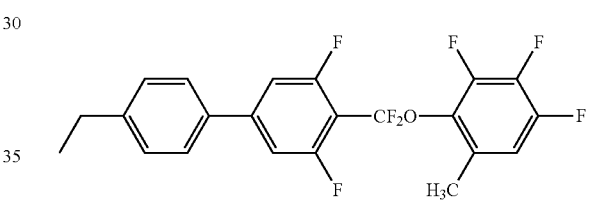

The parameters of PUQYi-2-F are as follows: Δn=0.1381, CP=31.3° C., ε$_\perp$=6.7 and Δε=11.8.

Example 3 PUQYii-3-F

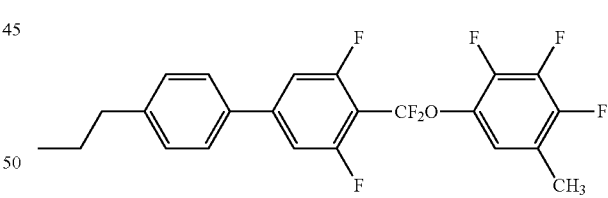

The parameters of PUQYii-3-F are as follows: Δn=0.1394, CP=30.1° C., ε$_\perp$=6.6 and Δε=12.0.

Example 4 PUQYi-3-O2

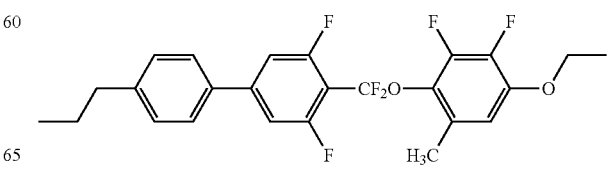

The parameters of PUQYi-3-02 are as follows: $\Delta n=0.1702$, $CP=71.0°$ C., $\varepsilon_\perp=7.9$ and $\Delta\varepsilon=1.2$.

Example 5 PUQYi-3-04

The parameters of PUQYi-3-04 are as follows: $\Delta n=0.1650$, $CP=67.2°$ C., $\varepsilon_\perp=8.8$ and $\Delta\varepsilon=0.2$.

Example 6 PGUQYi-3-F

The parameters of PGUQYi-3-F are as follows: $\Delta n=0.2105$, $CP=140.5°$ C., $\varepsilon_\perp=6.2$ and $\Delta\varepsilon=15.8$.

Example 7 PGUQYi-3-02

The parameters of PGUQYi-3-02 are as follows: $\Delta n=0.2307$, $CP=205.5°$ C., $\varepsilon_\perp=6.9$ and $\Delta\varepsilon=3.5$.

Example 8 APUQYi-3-F

The parameters of APUQYi-3-F are as follows: $\Delta n=0.1572$, $CP=123.6°$ C., $\varepsilon_\perp=6.4$, and $\Delta\varepsilon=14.2$.

Example 9 CPUQYi-3-F

The parameters of CPUQYi-3-F are as follows: $\Delta n=0.1502$, $CP=130.5°$ C., $\varepsilon_\perp=6.8$ and $\Delta\varepsilon=12.8$.

Liquid Crystal Composition Examples:

Example 10

| Category | Liquid crystal monomer code | Content (%) |
| --- | --- | --- |
| I | APUQYi-3-F | 10 |
| I | PUQYi-3-F | 10 |
| I | PGUQYi-3-F | 10 |
| I | PUQYi-3-O2 | 10 |
| II | CC-3-V | 30 |
| II | CC-3-V1 | 5 |
| II | CP-3-O2 | 5 |
| II | CCP-3-3 | 7 |
| II | CCP-V-1 | 8 |
| II | CPP-V1-2 | 5 |

$\Delta\varepsilon$[1 KHz, 25° C.]: 4.3
$\varepsilon_\perp$: 4.1
$\Delta n$[589 nm, 25° C.]: 0.1211
Cp: 88° C.
$\gamma_1$: 85 mPa · s.

After the composition of Example 10 is stored at −20° C. for 120 hours, there is also no precipitation of the crystal of the compound of formula I.

Example 11

| Category | Liquid crystal monomer code | Content (%) |
| --- | --- | --- |
| I | PUQYi-2-F | 5 |
| I | CPUQYi-3-F | 10 |
| I | PGUQYi-3-F | 10 |
| I | PUQYii-3-F | 5 |
| II | CC-3-V | 25 |
| II | CC-5-V | 5 |
| II | CP-3-O1 | 3 |
| II | PP-5-1 | 2 |
| II | CCP-2V-1 | 5 |
| III | CCP-3-F | 10 |
| III | CCU-3-F | 10 |
| III | CPU-3-F | 5 |
| III | PGP-C(3)1-3 | 5 |

$\Delta\varepsilon$[1 KHz, 25° C.]: 6.3
$\varepsilon_\perp$: 4.0
$\Delta n$[589 nm, 25° C.]: 0.1175
Cp: 85° C.
$\gamma_1$: 85 mPa · s.

After the composition of Example 11 is stored at −20° C. for 120 hours, there is also no precipitation of the crystal of the compound of formula I.

Example 12

| Category | Liquid crystal monomer code | Content (%) |
| --- | --- | --- |
| I | PGUQYi-3-O2 | 3 |
| I | PUQYi-3-O4 | 8 |
| I | PUQYi-3-O2 | 9 |
| II | CC-3-V | 30 |
| II | CC-2-3 | 5 |
| II | PP-1-5 | 5 |
| II | PP-2V-1 | 3 |
| II | CCP-3-1 | 2 |
| II | CPP-3-2V1 | 5 |
| III | CCG-3-F | 5 |

-continued

| Category | Liquid crystal monomer code | Content (%) |
|---|---|---|
| III | CGU-3-F | 5 |
| III | CCP-3-OT | 5 |
| III | PPGi-3-F | 5 |
| IV | PUQU-C(5)-F | 1 |
| IV | PUQU-C(3)1-F | 1 |
| IV | PGUQU-3-F | 1 |
| IV | PGUQU-C(3)-F | 2 |
| IV | PGUQU-C(5)-F | 2 |
| IV | CPUQU-C(5)-F | 3 |

Δε[1 KHz, 25° C.]: 4.1
$\varepsilon_\perp$: 4.2
Δn[589 nm, 25° C.]: 0.1195
Cp: 74° C.
$\gamma_1$: 88 mPa · s.

After the composition of Example 12 is stored at −20° C. for 120 hours, there is also no precipitation of the crystal of the compound of formula I.

Example 13

| Category | Liquid crystal monomer code | Content (%) |
|---|---|---|
| I | PUQYi-3-O2 | 7 |
| I | PGUQYi-3-F | 7 |
| I | PUQYi-3-F | 7 |
| I | PUQYii-3-F | 7 |
| I | PUQYi-2-F | 7 |
| II | CC-3-V | 10 |
| II | CC-V-V1 | 5 |
| II | PP-2V-1 | 7 |
| II | CCP-V-1 | 8 |
| III | PGU-3-F | 2 |
| III | CGU-3-F | 3 |
| III | CPUP-3-OT | 2 |
| III | PGP-3-F | 3 |
| IV | APUQU-C(5)-F | 10 |
| IV | DUQU-C(5)-F | 5 |
| IV | CPUQU-C(5)-F | 5 |
| V | CPY-3-O2 | 5 |

Δε[1 KHz, 25° C.]: 9.6
$\varepsilon_\perp$: 5.1
Δn[589 nm, 25° C.]: 0.1414
Cp: 78° C.
$\gamma_1$: 115 mPa · s.

After the composition of Example 13 is stored at −20° C. for 120 hours, there is also no precipitation of the crystal of the compound of formula I.

Example 14

| Category | Liquid crystal monomer code | Content (%) |
|---|---|---|
| I | PUQYi-2-F | 5 |
| I | PGUQYi-3-O2 | 2 |
| I | PUQYi-3-O4 | 3 |
| II | CC-3-V | 30 |
| II | CC-V-V1 | 20 |
| II | CPP-3-2 | 10 |
| II | CCP-V-1 | 5 |
| III | CPGU-C(5)-F | 2 |
| III | PPGU-C(5)-F | 3 |
| IV | PUQU-C(5)-F | 5 |
| IV | PGUQU-3-F | 5 |
| IV | CPUQU-C(5)-F | 5 |

-continued

| Category | Liquid crystal monomer code | Content (%) |
|---|---|---|
| V | CPY-3-O2 | 2 |
| V | CY-3-O4 | 3 |

Δε[1 KHz, 25° C.]: 4.9
$\varepsilon_\perp$: 3.8
Δn[589 nm, 25° C.]: 0.109
Cp: 80° C.
$\gamma_1$: 63 mPa · s.

After the composition of Example 14 is stored at −20° C. for 120 hours, there is also no precipitation of the crystal of the compound of formula I.

Example 15

| Category | Liquid crystal monomer code | Content (%) |
|---|---|---|
| I | PUQYi-3-O2 | 2 |
| I | PUQYi-3-F | 3 |
| II | CC-3-V | 20 |
| II | CCP-V-1 | 5 |
| III | CCU-4-F | 15 |
| III | CPUP-3-OT | 10 |
| III | CPU-5-F | 15 |
| IV | PUQU-C(5)-F | 10 |
| IV | PGUQU-3-F | 5 |
| IV | CPUQU-C(5)-F | 5 |
| V | CPY-3-O2 | 2 |
| V | CCY-3-O2 | 2 |
| V | PPY-3-O2 | 3 |
| V | COY-3-O2 | 3 |

Δε[1 KHz, 25° C.]: 9.2
$\varepsilon_\perp$: 4.7
Δn[589 nm, 25° C.]: 0.122
Cp: 90° C.
$\gamma_1$: 115 mPa · s.

The liquid crystal composition of Example 15 has a moderate Δε, a larger Δn, a lower $\gamma_1$ and an appropriate Cp, and is suitable for a liquid crystal material of a rapid response, a low cell thickness TN, IPS or FFS-TFT display. After the composition of Example 15 is stored at −20° C. for 120 hours, there is also no precipitation of the crystal of the compound of formula I.

Example 16

| Category | Liquid crystal monomer code | Content (%) |
|---|---|---|
| I | PGUQYi-3-F | 2 |
| I | PUQYi-3-F | 2 |
| I | PGUQYi-3-O2 | 1 |
| II | CC-3-V | 20 |
| II | CCP-V2-1 | 5 |
| III | CCU-4-F | 15 |
| III | CCG-4-F | 10 |
| III | CPU-5-F | 15 |
| IV | PUQU-C(5)-F | 10 |
| IV | PGUQU-3-F | 5 |
| IV | PGUQU-C(3)1-F | 5 |
| V | CPY-3-O2 | 5 |
| V | CCY-3-O2 | 5 |

Δε[1 KHz, 25° C.]: 8.9
$\varepsilon_\perp$: 4.6
Δn[589 nm, 25° C.]: 0.111
Cp: 87° C.
$\gamma_1$: 115 mPa · s.

The liquid crystal composition of Example 16 has a larger Δε, a larger Δn, a moderate Cp and a larger $\varepsilon_\perp$, and is suitable for a liquid crystal material of a high transmittance, a rapid response and a TN, IPS or FFS-TFT display.

After the composition of Example 16 is stored at −20° C. for 240 hours, there is also no precipitation of the crystal of the compound of formula I.

Example 17

| Category | Liquid crystal monomer code | Content (%) |
|---|---|---|
| I | APUQYi-3-F | 5 |
| I | PUQYi-2-F | 5 |
| I | PUQYi-3-F | 10 |
| II | CC-3-V | 31 |
| II | CCP-V-1 | 5 |
| III | CCU-4-F | 5 |
| III | CCP-2-OT | 2 |
| III | CPU-3-F | 5 |
| III | PGP-C(3)1-1 | 3 |
| III | PPGi-2-F | 3 |
| III | PGP-3-F | 4 |
| VI | PUQY-3-O4 | 10 |
| VI | PGUQY-3-O2 | 4 |
| VI | APUQY-3-O2 | 5 |
| VI | PUQY-3-F | 3 |

Δε[1 KHz, 25° C.]: 4.7
$\varepsilon_\perp$: 4.7
Δn[589 nm, 25° C.]: 0.122
Cp: 76° C.
γ₁: 110 mPa·s.

After the composition of Example 17 is stored at −20° C. for 240 hours, there is also no precipitation of the crystal of the compound of formula I.

Example 18

| Category | Liquid crystal monomer code | Content (%) |
|---|---|---|
| I | APUQYi-3-F | 5 |
| I | PUQYii-3-F | 5 |
| I | PGUQYi-3-F | 10 |
| II | CC-3-V | 31 |
| II | CC-3-V1 | 5 |
| III | CCU-4-F | 5 |
| III | CCP-2-OT | 2 |
| III | CPU-3-F | 5 |
| III | CPUP-3-OT | 3 |
| III | PPGU-C(5)-F | 3 |
| V | CPY-3-O2 | 4 |
| VI | PUQY-3-O4 | 10 |
| VI | PGUQY-3-O2 | 4 |
| VI | APUQY-3-O2 | 5 |
| VI | PUQY-3-F | 3 |

Δε[1 KHz, 25° C.]: 5.2
$\varepsilon_\perp$: 4.0
Δn[589 nm, 25° C.]: 0.1105
Cp: 84° C.
γ₁: 75 mPa·s.

After the liquid crystal composition of Example 18 is stored at −20° C. for 240 hours, there is also no precipitation of the crystal of the compound of formula I.

Example 19

| Category | Liquid crystal monomer code | Content (%) |
|---|---|---|
| I | PUQYi-3-F | 15 |
| II | CC-3-V | 36 |
| II | CCP-V2-1 | 5 |
| III | CCP-3-F | 5 |
| III | CCP-2-OT | 7 |
| III | CCG-5-F | 5 |
| IV | APUQU-C(5)-F | 3 |
| IV | PGUQU-C(5)-F | 2 |
| IV | PGUQU-C(3)1-F | 3 |
| V | CPY-3-O2 | 5 |
| VI | PUQY-3-O4 | 2 |
| VI | PGUQY-3-O2 | 4 |
| VI | APUQY-3-O2 | 5 |
| VI | PUQY-3-F | 3 |

Δε[1 KHz, 25° C.]: 5.1
$\varepsilon_\perp$: 4.4
Δn[589 nm, 25° C.]: 0.1056
Cp: 85° C.
γ₁: 105 mPa·s.

After the liquid crystal composition of Example 19 is stored at −20° C. for 240 hours, there is also no precipitation of the crystal of the compound of formula I.

Comparative Example 1

The PUQYi-3-F compound in Example 10 is replaced with a PUQY-3-F compound in the prior art; the $\varepsilon_\perp$ data is reduced to 3.8 and the Cp is reduced to 86° C.; after the liquid crystal composition is placed in a flask at −20° C. and maintained for 100 hours, the PUQY-3-F is precipitated;

Comparative Example 2

The 10% PGUQYi-3-F compound of formula I in Example 10 is replaced with PGUQY-3-F; the $\varepsilon_\perp$ data is 3.9 and the Cp is reduced to 85° C.; after being maintained at −20° C. for 100 hours, the PGUQY-3-F is precipitated; and Comparative Example 3

The 10% PUQYi-3-O2 compound of formula I in Example 10 is replaced with PUQY-3-O2; the $\varepsilon_\perp$ data is 3.7 and the Cp is reduced to 87° C.; after being maintained at −20° C. for 100 hours, the PUQY-3-O2 is precipitated.

The invention claimed is:

1. A difluoromethoxy-bridge liquid crystal compound containing methyl-substituted 2,3-difluorophenyl, represented by formula I3, I5 to I18,

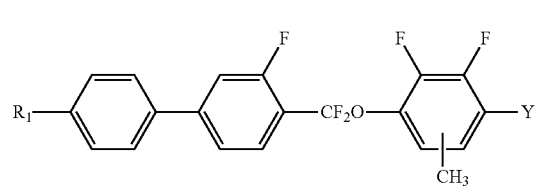

I5
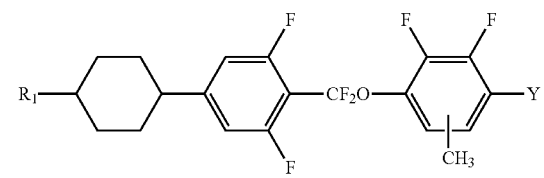

I6
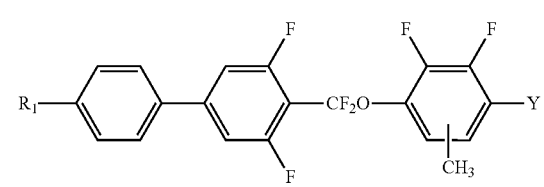

I7
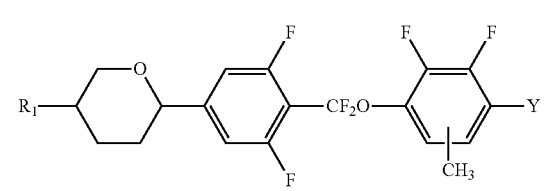

I8
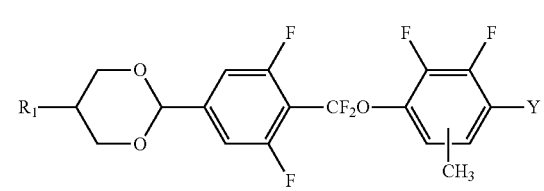

I9
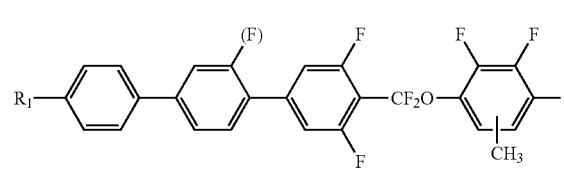

I10
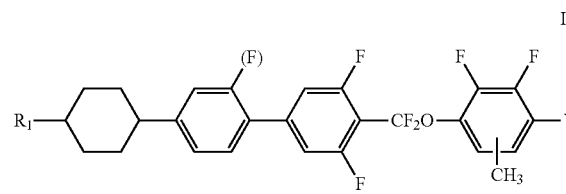

I11
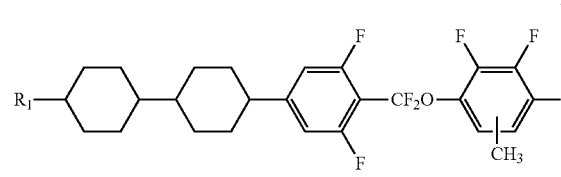

I12
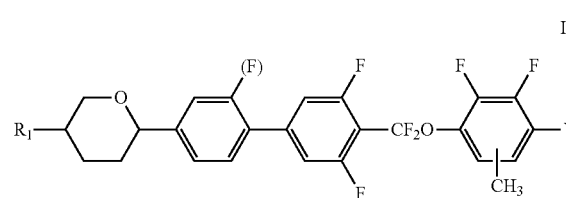

I13

I14
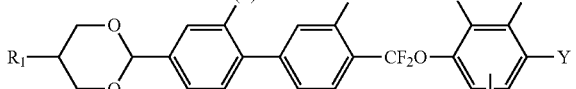

I15

I16
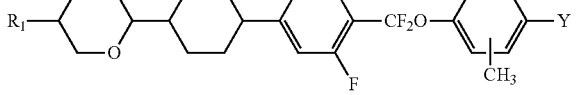

I17
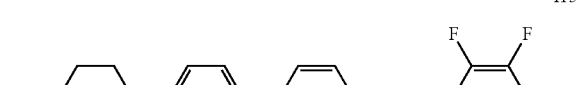

I18

wherein $R_1$ represents H, an alkyl group having a carbon atom number of 1-5, an alkenyl group having a carbon atom number of 2-6 or an alkoxy group having a carbon atom number of 1-5, with any $CH_2$ in $R_1$ being optionally substituted with cyclopentyl, cyclobutyl or cyclopropyl, any $CH_2$ not connected to O being optionally substituted with O and any one or more hydrogen atoms being optionally replaced with fluorine atom; and Y represents H, F, Cl, CN, an alkyl group having a carbon atom number of 1-5, an alkenyl group having a carbon atom number of 2-6 or an alkoxy group having a carbon atom number of 1-5, with any $CH_2$ not connected to O being optionally substituted with O and any one or more hydrogen atoms being optionally replaced with fluorine atom;

represents

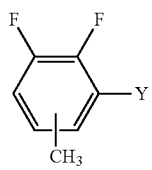

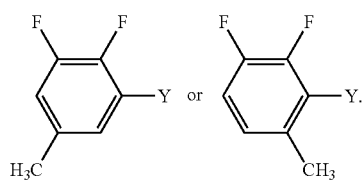

2. A liquid crystal composition, wherein said liquid crystal composition comprises one or more difluoromethoxy-bridge liquid crystal compounds containing methyl-substituted 2,3-difluorophenyl of claim 1.

3. The liquid crystal composition according to claim 2, wherein said liquid crystal composition further comprises one or more compounds represented by formula II,

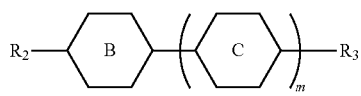

wherein $R_2$ and $R_3$ each independently represent an alkyl group having a carbon atom number of 1-5, an alkenyl group having a carbon atom number of 2-6 or an alkoxy group having a carbon atom number of 1-5;
m represents 1 or 2;
and

and

each independently represent one or more selected from phenylene, cyclohexylene and cyclohexenylene.

4. The liquid crystal composition according to claim 3, wherein the content in mass percentage of the compound represented by formula I is 1-40%, and the content in mass percentage of the compound represented by formula II is 1-65%.

5. The liquid crystal composition according to claim 3, wherein said one or more compounds represented by formula II are selected from the group consisting of compounds represented by formulas II1 to II22 below:

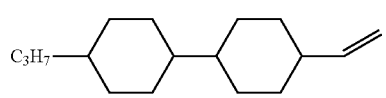

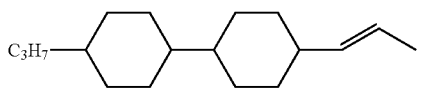

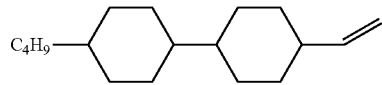

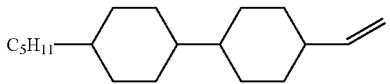

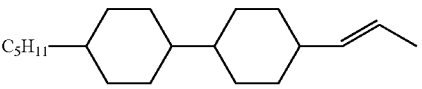

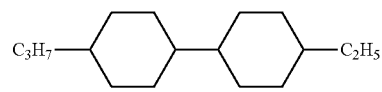

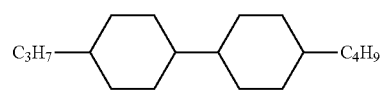

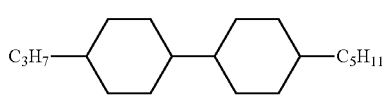

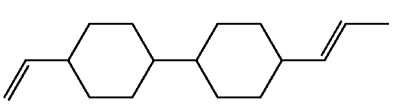

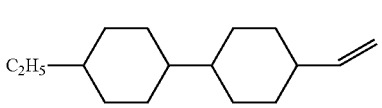

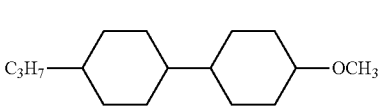

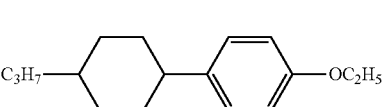

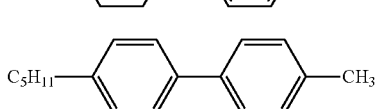

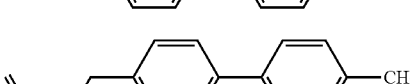

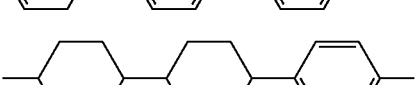

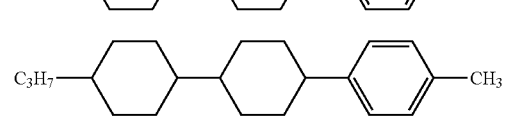

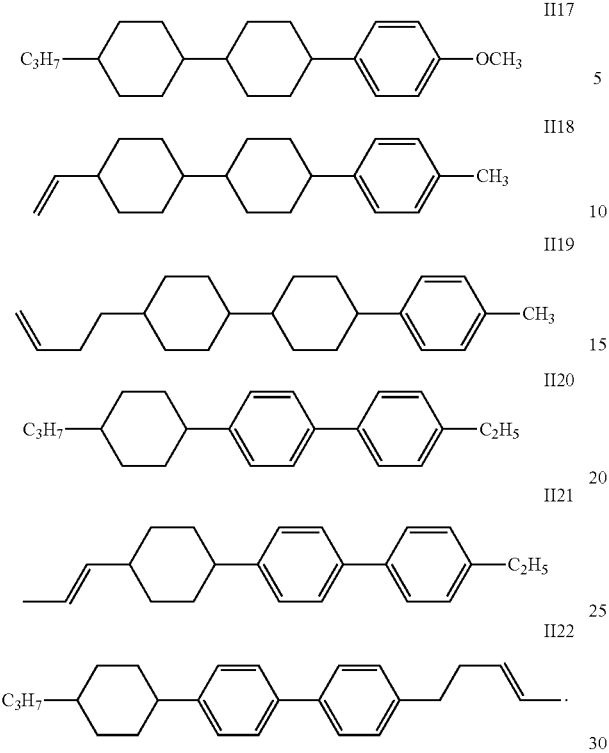
6. The liquid crystal composition according to claim 2, wherein said liquid crystal composition comprises one or more of compounds represented by formulas III1 to III14 below:
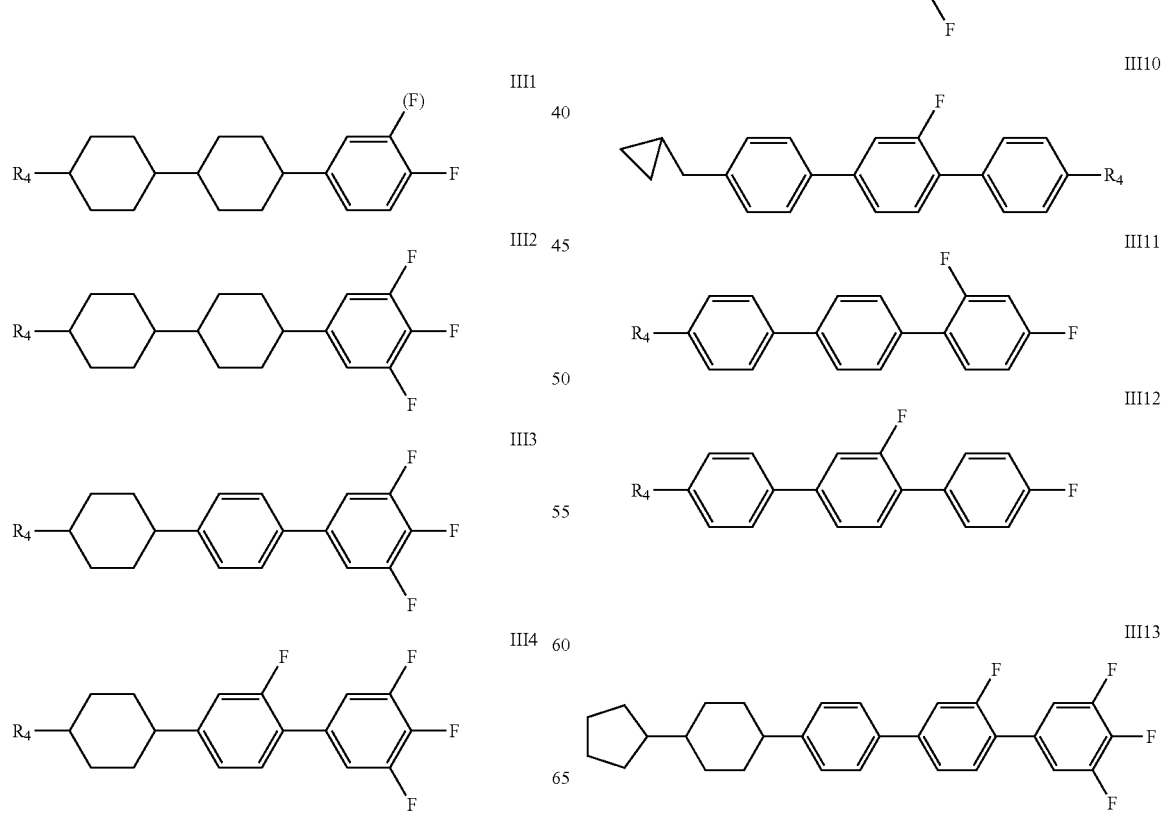

III14

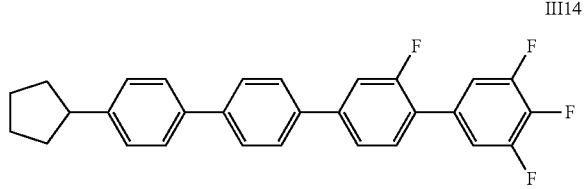

R$_4$ represents H, an alkyl group having a carbon atom number of 1-5, an alkenyl group having a carbon atom number of 2-6 or an alkoxy group having a carbon atom number of 1-5, with any CH$_2$ in R$_4$ being optionally substituted with cyclopentyl, cyclobutyl or cyclopropyl;

(F) represents F or H;

and (O) represents —O— or a single bond.

7. The liquid crystal composition according to claim 2, wherein said liquid crystal composition further comprises one or more compounds represented by formula IV,

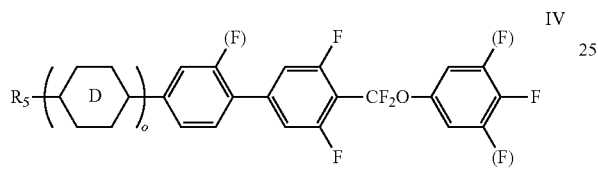

IV

R$_5$ represents H, an alkyl group having a carbon atom number of 1-5, an alkenyl group having a carbon atom number of 2-6 or an alkoxy group having a carbon atom number of 1-5, with any CH$_2$ in R$_5$ being optionally substituted with cyclopentyl, cyclobutyl or cyclopropyl;

o represents 0 or 1;

represents phenylene, cyclohexylene, cyclohexenylene or a group formed by substituting one or two non-connected CH$_2$ in cyclohexylene with O;

and (F) each independently represents H or F.

8. The liquid crystal composition according to claim 2, wherein said liquid crystal composition further comprises one or more negative compounds represented by formula V,

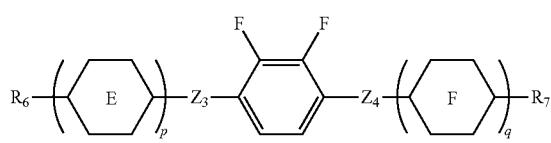

V wherein R$_6$ and R$_7$ represent H, an alkyl group having a carbon atom number of 1-5, an alkenyl group having a carbon atom number of 2-6 or an alkoxy group having a carbon atom number of 1-5, with any CH$_2$ in R$_6$ and R$_7$ being optionally substituted with cyclopentyl, cyclobutyl or cyclopropyl;

p and q each independently represent 0, 1 or 2, with 1≤p+q≤3;

Z$_3$ and Z$_4$ each independently represent a single bond, —CH$_2$CH$_2$—, —CH$_2$O— or —OCH$_2$—; and

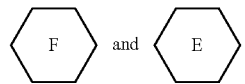

each independently represent one or more of

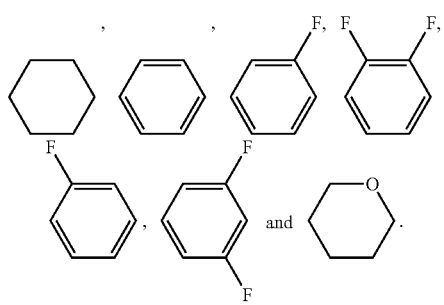

9. The liquid crystal composition according to claim 2, wherein said liquid crystal composition further comprises one or more compounds represented by formula VI

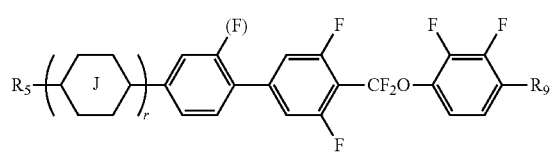

VI wherein R$_8$ represents H, an alkyl group having a carbon atom number of 1-5, an alkenyl group having a carbon atom number of 2-6 or an alkoxy group having a carbon atom number of 1-5, with any CH$_2$ in R$_8$ being optionally substituted with cyclopentyl, cyclobutyl or cyclopropyl;

represents phenylene, cyclohexylene, cyclohexenylene or a group formed by substituting one or two non-connected CH$_2$ in cyclohexylene with O;

r represents 0 or 1;

(F) represents F or H;

and R$_9$ represents F, an alkyl group having a carbon atom number of 1-6 or an alkoxy group having a carbon atom number of 1-6.

10. A liquid crystal display element or liquid crystal display comprising a liquid crystal compound of claim 1, wherein said liquid crystal display element or liquid crystal display is an active matrix display element or liquid crystal display, or a passive matrix display element or liquid crystal display.

* * * * *